United States Patent [19]
Elghazzawi

[11] Patent Number: 5,819,007
[45] Date of Patent: Oct. 6, 1998

[54] FEATURE-BASED EXPERT SYSTEM CLASSIFIER

[75] Inventor: Ziad F. Elghazzawi, Medford, Mass.

[73] Assignee: Siemens Medical Systems, Inc., Iselin, N.J.

[21] Appl. No.: 616,362

[22] Filed: Mar. 15, 1996

[51] Int. Cl.⁶ .......................... G06F 15/18; A61B 5/0464
[52] U.S. Cl. ................................ 395/51; 706/45; 706/12; 706/52; 128/702
[58] Field of Search ....................... 395/61, 51; 382/228; 128/702, 705; 607/14

[56] References Cited

U.S. PATENT DOCUMENTS

| | | | |
|---|---|---|---|
| 5,193,550 | 3/1993 | Duffin ...................................... | 128/705 |
| 5,361,379 | 11/1994 | White ....................................... | 395/61 |
| 5,365,426 | 11/1994 | Siegel et al. ............................. | 128/702 |
| 5,400,795 | 3/1995 | Murphy et al. .......................... | 128/702 |
| 5,455,892 | 10/1995 | Minot et al. .............................. | 395/23 |
| 5,493,729 | 2/1996 | Nigawara et al. ........................ | 395/61 |
| 5,545,186 | 8/1996 | Olson et al. .............................. | 607/14 |

OTHER PUBLICATIONS

S. Georgeson and H. Warner, "Expert System Diagnosis of Wide Complex Tachycardia," Computers in Cardiology, pp. 671–674, Oct. 1992.

T.R. Turner, et al., "Statistical Discriminant Analysis of Arrhythmias using Intracardial Electrograms," IEEE Trans. on Biomedical Engineering, vol. 40 (9), pp. 985–989, Sep. 1993.

A. Taddei, et al., "ABACUS: A Knowledge–Based System for the Interpretation of Arrhythmias in Long Term ECG," Computers in Cardiology, pp. 887–890, Sep. 1993.

E. Chowdhury and L.C. Ludeman, "Discrimination of Cardiac Arrhythmias Using a Fuzzy Rule–Based Method," Computers in Cardiology, pp. 549–552, Sep. 1994.

J.N. Froning, et al., "Classification of CAD Severity Using Fusion Neural Net Analysis of Multiple Exercise ECG Waveform Representations," Computers in Cardiology, pp. 605–608, Sep. 1994.

J. Ge, et al., "An Intelligent System for Electrocardiogram Diagnosis," Engineering in Medicine & Biology, vol. 2, pp. 1376–1377, Nov. 1994.

D.T. Thomson, et al., "Fuzzy Logic Classification of Fragmented Cardiac Myopotentials," 1994 Int'l. Conf. on Engineering in Medicine & Biology, vol. 2, pp. 1380–1381, Nov. 1994.

"Neural Network for automatic Anomalous QRS Complex Detection", Casaleggio et al., Proceedings, Computers in Cardiology (Cat. No. 90CH3011–4), 23–26 Sep. 1990, Chicago, IL, USA, pp. 553–556.

(List continued on next page.)

*Primary Examiner*—Robert W. Downs
*Attorney, Agent, or Firm*—Lawrence C. Edelman

[57] ABSTRACT

A method and apparatus for classifying an input as belonging to one of a plurality of predefined classes, comprises: (a) developing a plurality of feature values and forming a feature vector from the feature values which is representative of the input, (b) applying the feature vector to a knowledge-base comprising predictivity curves for each class of said plurality of classes, and developing a plurality of predictivity values for each feature, each predictivity value being indicative of a likelihood of the input belonging to a respective one of each of said classes based on the feature value; (c) combining the predictivity values developed for each of the features for each class to generate a total predictivity value for each class; and (d) generating a determination of class based upon the total predictivity values generated by the prior step.

28 Claims, 13 Drawing Sheets

OTHER PUBLICATIONS

"On Using Causal Knowledge to Recognize Vital Signs: Knowledge–Based Interpretation of Arrhythmias", T. Shibahara, Int'l Joint Conference on Artificial Intelligence, 1985, pp. 307–314.

"Rule–Based Learning for More Accurate ECG Analysis", K. Birman, IEEE Transactions on Pattern Analysis and Machine Intelligence, vol. PAMI–4, No. 4, July 1982, pp. 369–380.

"Grammatic Representation of Beat Sequences for Fuzzy Arrhythmia Diagnosis", Barro et al., Int. J. Biomed. Comput., 27(1991), pp. 245–259.

"Arrhythmia Monitoring Using Fuzzy Reasoning", Barro et al., Annual Int'l. Conf. of IEEE Engineering in Medicine and Biology Society, vol. 12, No. 2, 1990, pp. 823–824.

"Quantitative Models for Reasoning under Uncertainty in Knowledge–Based Expert Systems", Lee et al., Int'l Journal of Intelligent Systems, vol. II, (1987), pp. 15–38.

abs (CURRENT BEAT POL.-NORMAL BEAT POL.)

abs (CURRENT BEAT POL.-NORMAL BEAT POL.)

FEATURE-BASED EXPERT SYSTEM CLASSIFIER

BACKGROUND

1. Field of the Invention

The present invention relates to use of an expert system for determining a classification for an input which is definable by a set of features, and in particular, to an expert system for classifying the QRS component of the heartbeat of a patient to a given beat label (e.g., Normal, Ventricular, or X (Unknown)) using a knowledged-based expert system.

2. Description of the Prior Art

The classification of ECG (electrocardiogram) beats has been a constant challenge for system design and development engineers in the field of patient monitoring. Over the years the purpose of ECG monitoring has changed from simple periodic scanning of the ECG signal on an oscilloscope, in the 1960's, to ST segment monitoring and sophisticated arrhythmia detection in the present. The original clinical purpose of monitoring ECG traces in coronary care units (CCU's) was to detect catastrophic events, like ventricular fibrillation (VF) and asystole in patients who are admitted with a condition of myocardium infarction. Now, the goal of ECG monitoring is to detect the occurrence of premature ventricular beats (PVB) and then promptly treat them, because it is believed that the occurrence of these PVB's can be the preset of ventricular fibrillation. Ventricular fibrillation can result in sudden death if not treated immediately. Since PVB occurrence can be suppressed by antiarrhythmic drugs, and thus suppressing the occurrence of ventricular fibrillation, it is important to detect PVB's and treat the patient as soon as possible as a preventive measure.

Existing monitoring systems typically classify an ECG beat as one of either Normal (N) or Ventricular(V). Based on the beat classification, cardiac rhythms are identified and in the event a dangerous condition is monitored, alarms are generated for alerting the clinical staff. For proper care of the patient, in the event of an alarm the response of the clinical staff must be fast. If the sensitivity of the detection of these cardiac rhythms is low, some of the life threatening alarms can be missed, greatly compromising the care of the patient. On the other hand, if the sensitivity is too high, leading to a high rate of false alarms, the clinical staff will become desensitized to these alarms, again compromising the care of the patient. False alarms may also result in mistreating a patient by administering an overdose of anti-arrhythmic drugs. The ideal patient monitor should provide for arrhythmia detection in a manner that has both high sensitivity and a low rate of false alarms.

Early electronic arrhythmia detectors used analog circuits to store one normal QRS shape and compared other beats to this stored QRS shape, in addition to determining prematurity from the R-to-R interval (a heart rate meter). The shape matching technique works well when QRS shapes do not change due to cardiac axis shift or the presence of artifacts. However, in the case of a cardiac axis shift, the classifier must adapt the stored QRS shape to the new shape. However, this adaptation proved impossible to accomplish accurately with analog circuits. These early techniques were primitive and caused many false alarms which often motivated the clinical staff to disable the monitor alarms or set them to extreme limits that would only detect ventricular fibrillation and asystole.

With the digital era came software based arrhythmia detectors. Since the early seventies, only two basic techniques for arrhythmia detection have been in use: cross-correlation and feature extraction. The cross-correlation technique consists of taking a fixed window of waveform sample around the QRS portion of the ECG waveform and cross-correlating it with an adaptive dominant normal QRS window which has been previously learned. The feature extraction technique uses certain attributes (features) of the ECG signal for the determination of abnormal shapes. These features, normally measured values, are used to group QRS's into clusters based on similarity, and classify beats based on these clusters. Although there have been many improvements in arrhythmia detectors using these cross-correlation and/or feature extraction techniques, these changes only relate to the set of features used and/or the rules applied to the these features. For example, as will next be described, since the early 1980's expert systems and neural networks have been considered for use in the arrhythmia detection field. Hidden Markov Models were introduced in the mid-eighties, but are rarely used. The application of fuzzy logic to the arrhythmia detection problem has also been investigated.

Generally, all of the conventional techniques mentioned above, including expert systems and neural networks, still suffer, albeit to different degrees, from various disadvantages. For example, those having binary classification rules suffer from a limited dynamic range of the classifier, due to the use of the binary classification rules. That is, the classification rules are usually of the form "if A>B then C else D", where: A can be a measurement value of a feature, a correlation coefficient, or a distance measurement between clusters; and B is a threshold value, usually tuned and set subjectively by the designer (for all techniques except neural networks and fuzzy logic). C and D are the outcomes of the classification. The single threshold (B) divides the feature space into two sections: the first section represents features smaller than B and the second section represents features larger than B. Thus, the rule structure "if A>B" has a binary outcome: {0} if A is less than B, or {1} if A is larger than B. This binary outcome necessarily limits the dynamic range of the classifying rule and hence the performance of the classifier is undesirably affected.

Furthermore, although current systems typically use a direct method for beat classification in order to accomplish the classification in real-time (where the set of data that is currently being processed must be completed before the next set is introduced), a problem is presented by the use, of subjective or heuristically determined rules. That is, classification errors can easily occur when a patient presents ECG beats to a classifier that are of a shape that had never been considered before.

In recent years attempts have been made to use neural networks for ECG beat classification to overcome these limitations, since they employ principle (i.e., machine) learning and don't use "if A>B"-like statements. Neural networks consist of simple processing elements arranged in "feed-forward" layers that are densely interconnected, Each processing element can have multiple input signals, but produces only one output, which is a weighted sum of all its inputs. Knowledge of the patterns to be classified is stored in, or represented by, the values of the weights associated with the interconnections of the networks's elements. These weight values are determined by principle learning, using an iterative training process, such as back propagation, in accordance with a particular learning rule. The learning is said to be complete when the mean square error between the desired output and the actual input is minimized. For ECG applications, these neural networks are trained off-line on large sets of annotated ECG data, and then tested on a small set of data. Of particular relevance is research using a standard arrhythmia database, such as the MIT-BIH and AHA databases, for training and testing of ECG algorithms and for which statistical results are reported. The work of Casaleggio et al., for example, published in the Proceedings, Computers in Cardiology, Conference date 23–26 Sep. 1990, Chicago, Ill., USA, is representative of this work.

Comparison of the classification results between neural networks and conventional algorithms illustrate that the use of conventional algorithms for ECG beat classification is still more desirable because they generally score higher in sensitivity and accuracy than neural networks. An additional reason for their undesirability is that the end result of the network's back propagation learning process is merely a collection of weights for each of the nodal connections. Thus, the weights have no extrinsic meaning, and are therefore unable to be intelligently modified in order to attempt to improve the performance of the classifier. Furthermore, it is not even clear when the learning process is complete, since even the end point of the network's learning is subjectively determined by the designer, i.e., a global convergence of the learning is not guaranteed. Even further, although the performance of the classifier may be adequate when tested using the information it was trained on, poor performance can easily result when using new, real-world information because the system learning set did nit include data similar to the new data.

As noted above, expert systems have also been used for arrhythmia detection, but currently they still suffer some serious limitations. In general, an expert system can be considered an algorithm that makes decisions based on knowledge and facts. Decisions are made by testing hypothesis and weighing their evidence. The hypothesis with the maximum evidence in its favor usually wins and drives the decision process. The procedures employed for driving the decision process are either ad hoc or borrowed from statistical theory due to the lack of a knowledge-based decision theory. In construction, expert systems consist of a knowledge base and an inference engine. Application of an input, evidence, to the knowledge base results in knowledge being applied to the inference engine, allowing the engine to make a decision based on the knowledge.

The knowledge base consists of knowledge representation structures: logical representation, production rule representation, semantic network representation, frame representation, or combinations of these structures. A detailed discussion of these techniques is beyond the scope of this description, however one can refer, for example, to an article by T. Shibahara titled "On Using Causal Knowledge to Recognize Vital Signs: Knowledge-Based Interpretation of Arrhythmias", published in the International Joint Conference on Artificial Intelligence, pp. 307–314, 1985, for description of an expert system having a frame representation for the knowledge base. In Shibahara the knowledge base is stratified, each stratification representing a different perspective of the phenomenon to be classified. The biggest disadvantage of Shibahara's expert system is that the feature vector is derived from the sequence of P, Q, R, S, and T segments of the ECG waveform. If any of these segments is absent, this expert system will not function.

A good example of a rule-based inference system based on semantic representation to detect and classify ECG beats can be found in the work of K. Birman in the article titled "Rule-Based Learning for More Accurate ECG Analysis", published in IEEE Transaction on Pattern Analysis and Machine Intelligence, Volume PAMI-4, No. 4, July 1982. QRS morphologies are recognized hierarchically by segmenting each QRS complex using AZTEC encoding. Subsequent classification of QRS complexes is accomplished by matching the QRS segments to stored segments and using probability inference based on this matching. The main disadvantage of this technique is the heuristically determined matching procedure, as well as the use of heuristically determined probability inferences.

Expert systems employ in the inference engine several techniques to deal with uncertainty. Some of these techniques are: Bayesian decision theory, Dempster-Shafer belief functions, MYCIN confirmation and dis-confirmation models, and fuzzy logic. Again, a detailed discussion of these techniques is beyond the scope of this description, however one can refer, for example, to the work of S. Barro et al in the article titled "Grammatic Representation of Beat Sequences for Fuzzy Arrhythmia Diagnosis". Int. J. Biomed. Comput., 27 (1991), pp. 245–259 for application of fuzzy logic techniques to a production rule knowledge based expert system. As described therein, the system uses linguistic fuzzy variables, i.e., conditional "IF/THEN with a certainty" type statements. However, this technique, as well as all the other known expert systems, are rule-based, and therefore inherently subjective to the person who set up the rules. As previously noted, a knowledge base acquired heuristically is prone to errors due to the subjective nature of the system design. Additionally, as also noted above, the use of binary logic classification rules in expert systems that don't employ fuzzy logic (like "if A>B"), undesirably limits the dynamic range of the classifier, leading to a shallow knowledge of the problem domain.

The use of fuzzy logic techniques have been applied to overcome the dynamic range limitation imposed by binary classification rules, by using fuzzy (analog like) membership functions to replace the "if A>B"-like statements. However, these techniques still use heuristic learning, in that the fuzzy memberships are subjectively defined by designers.

It would be desirable to provide a classifier that would operate in real-time and make a more accurate classification than the classifiers that are now available. To do so, binary logic classification rules will have to be avoided, as well as heuristic learning of the knowledge base. Furthermore, whatever rules are used for classification, they should be arranged for parallel combination, unlike the serial (or tree) structure of the prior art, wherein one error can easily lead to an erroneous classification.

SUMMARY OF THE INVENTION

In accordance with the principles of the present invention, a method for classifying an input as belonging to one of a plurality of predefined classes, comprises: (a) developing a plurality of feature values and forming a feature vector from the feature values which is representative of the input, (b) applying the feature vector to a knowledge-base comprising predictivity curves for each class of said plurality of classes, and developing a plurality of predictivity values for each feature, each predictivity value being indicative of the input belonging to a respective one of each of said classes based on the feature value; (c) combining the predictivity values developed for each of the features for each class to generate a total predictivity value for each class; and (d) generating a determination of class based upon the total predictivity values generated by the prior step.

In accordance with one aspect of the invention the knowledge-base comprises a plurality of positive predictivity curves, one for each feature for each of the plurality of classes. The use of predictivity curves in place of binary rules results in an improved dynamic range performance for the classifier.

In accordance a further aspect of the invention the determination of class is made by comparing the total positive predictivity value determined for each class and selecting as the determined class that class having the greatest positive predictivity value. Thus, a serial application of the rules is avoided, thereby reducing erroneous classifications.

In accordance with a still further aspect of the invention a normal value for at least one of the features is developed using prior values of said feature that have previously been classified as normal, and a normalized feature value is developed for use in step (b) above, using the normalized value determined for that feature.

In accordance with an even further aspect of the invention the input vector is representative of a waveform and one of the feature values used in step (b) above is a value determined by the shape of the waveform matching a predetermined shape.

In accordance with an even further aspect of the invention, the knowledge base of predictivity curves for each of the plurality of classes is acquired via principle learning, thereby avoiding a heuristic learning and resulting in a deeper and broader knowledge of the problem domain.

In general, a classifier in accordance with the present invention uses a knowledge-based expert system engine which greatly improves the classification process. In the preferred embodiment the invention is used for classifying ECG heartbeat signals, although it should be clear that any classifiable input able to be represented by features capable of being measured can be classified using the present invention. The new classifier uses analog like (fuzzy) thresholds, the curves of predictivity values) instead of binary thresholds for its rules (inferences), and therefore, as shown in the preferred embodiment, presents a more logical approach of where to draw the line between beat classifications, such as Normal and Ventricular beats.

More specifically, in the present invention, membership functions, continuous curves of positive predictivity, are defined for each feature, which act as the rules for the classifier. In the illustrated embodiment the membership functions are derived from an annotated data set from a known, predetermined, database, i.e., the MIT-BIH arrhythmia database (available at the Massachusetts Institute of Technology, 77 Massachusetts Avenue, Room 20A-113, Cambridge, Mass. 02139, or the American Heart Association (AHA) arrhythmia database (available at ECRI, 5200 Butler Pike, Plymouth Meeting, Pa. 19462. Thus, the present invention represents a significant departure from the prior art in that: 1) the knowledge-base (continuous curves of positive predictivity) is acquired via principle, rather than heuristic learning, and 2) there is no single threshold for any given rule, since continuous curves act as the rules for the classifier. These two features of the new classifier greatly improve it's performance.

Additionally, a third feature of the new classifier is it's advantageous use of a parallel structure for combining the information acquired from the knowledge-base, instead of a serial structure as used by the prior art, thereby reducing the occurrence of false labeling of beats. That is, by using a parallel combination of the acquired knowledge (the summation of the predictivity values), as compared to the serial (or tree) rule structure of the prior art, one error in the decision process does not lead to a false label.

DETAILED DESCRIPTION OF THE PREFERRED EMBODIMENT

General Description

Figure 1:
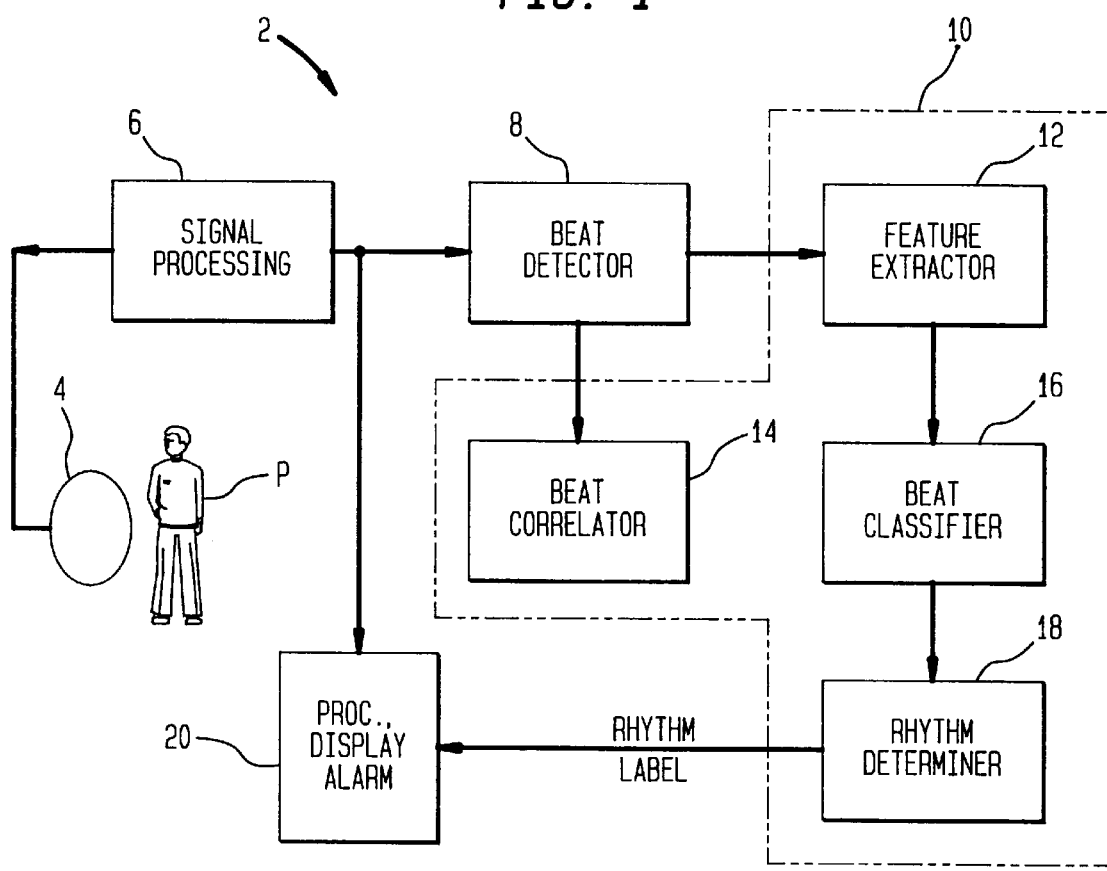
FIG. 1 illustrates in block diagram form the general structure of a patient monitor having an arrhythmia detector.

As shown in FIG. 1, a patient monitor 2 includes a sensor arrangement 4, typically a plurality of electrodes, mounted on a patient P for acquiring low-level electrocardiographic (ECG) signals representative of the heartbeat of the patient. Front-end signal processing circuitry 6, well known to those of ordinary skill in the art, is where the ECG signal is filtered, typically using a bandpass filter of, e.g., 0.5–40 Hz, and amplified. Additionally, pacemaker pulses are normally detected at this stage. The filtered and amplified ECG signal is then applied to a conventional beat detector 8, which detects the QRS portion of the ECG signals using e.g., one of a signal amplitude threshold crossing or filter matching technique. The detected QRS's are then analyzed by an arrhythmia detector 10 for classifying the detected QRS's, for example, as normal (N) or ventricular (V), and then developing a heartbeat rhythm label.

In the illustrated embodiment detector 10 includes both a feature extractor 12 and a beat correlator 14. In feature extractor 12 a measurement value for features such as QRS width, amplitude, polarity, area, r-r interval, etc. are determined (extracted) and applied to a beat classifier 16 for determining a classification of the detected QRS based on the value of the extracted features. Beat correlator 14 is used to develop an additional input to classifier 16, which input is a value representative of the degree of matching of the shape of the current QRS to the shape of the current dominate normal (CDN) QRS, which value is determined by template matching, (e.g., cross-correlation) of the current QRS with a learned CDN. Classifier 16 provides at its output a beat classification (label) for the current QRS based on application of predetermined rules to the feature values presented to its input. A rhythm determiner 18, of conventional design, determines a rhythm for the ECG signal based on the frequency and sequence of the QRS classifications provided by beat classifier 16. The remainder of the patient monitor comprises conventional signal processing, display and alarm circuitry 20, for causing display of the patient's ECG signal, and when a dangerous ECG rhythm is determined by detector 10, causing an alarm (visual and/or audible) to be generated. As described so far, the detector 10 is constructed and operates in a manner well known to those of ordinary skill in this technology.

Figure 2:
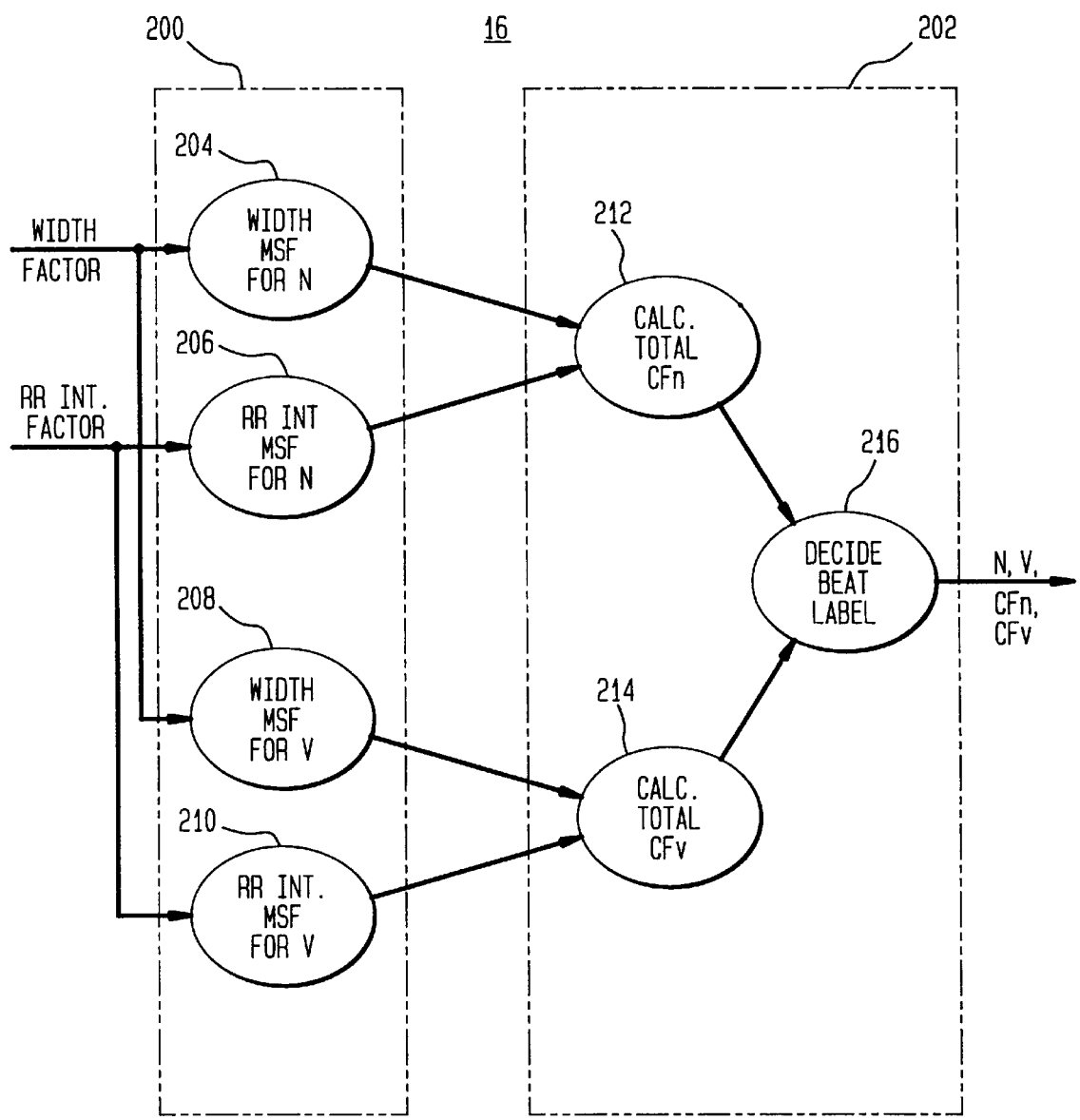
FIG. 2 illustrates a concept diagram of an expert system arrhythmia detector constructed in accordance with the principles of the present invention.
Figure 3:
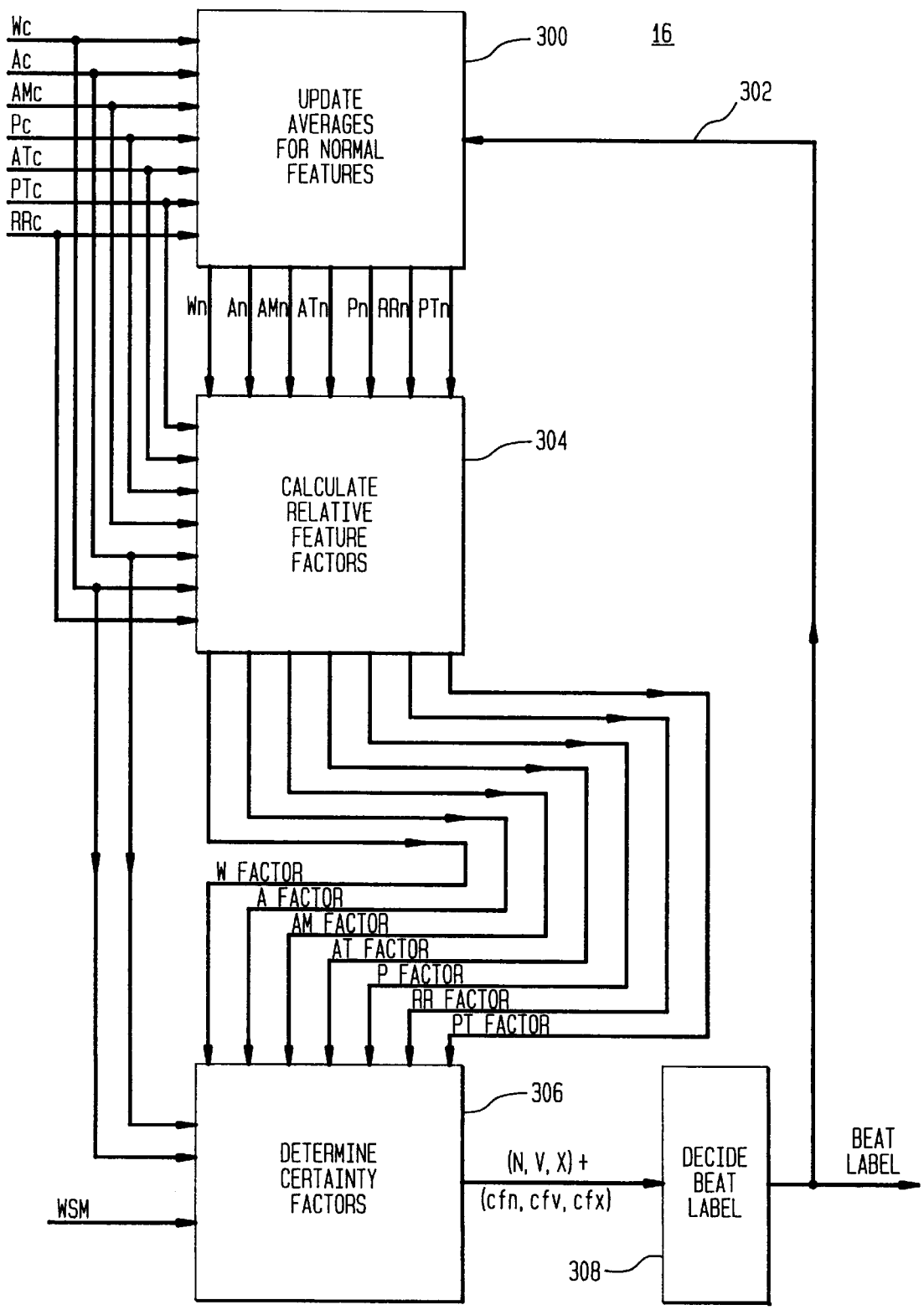
FIG. 3 illustrates in block diagram form the structure of the arrhythmia detector shown in FIG. 2.
Figure 4:
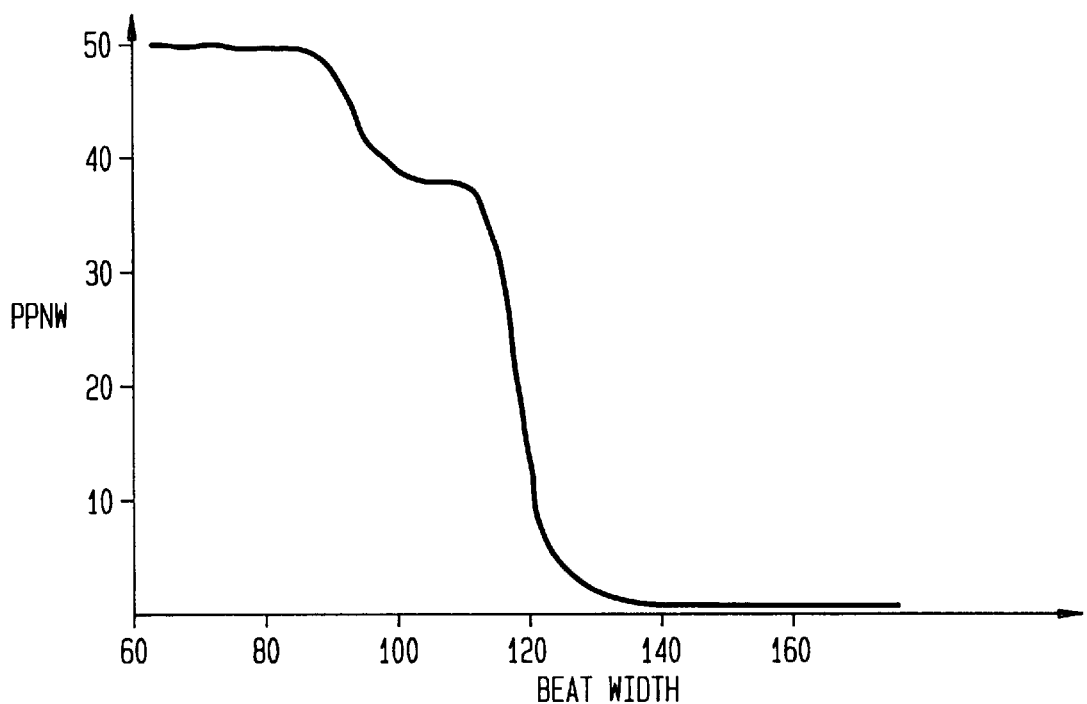
FIGS. 4–23 illustrate certainty curves useful for understanding operation of the present invention.
Figure 5:
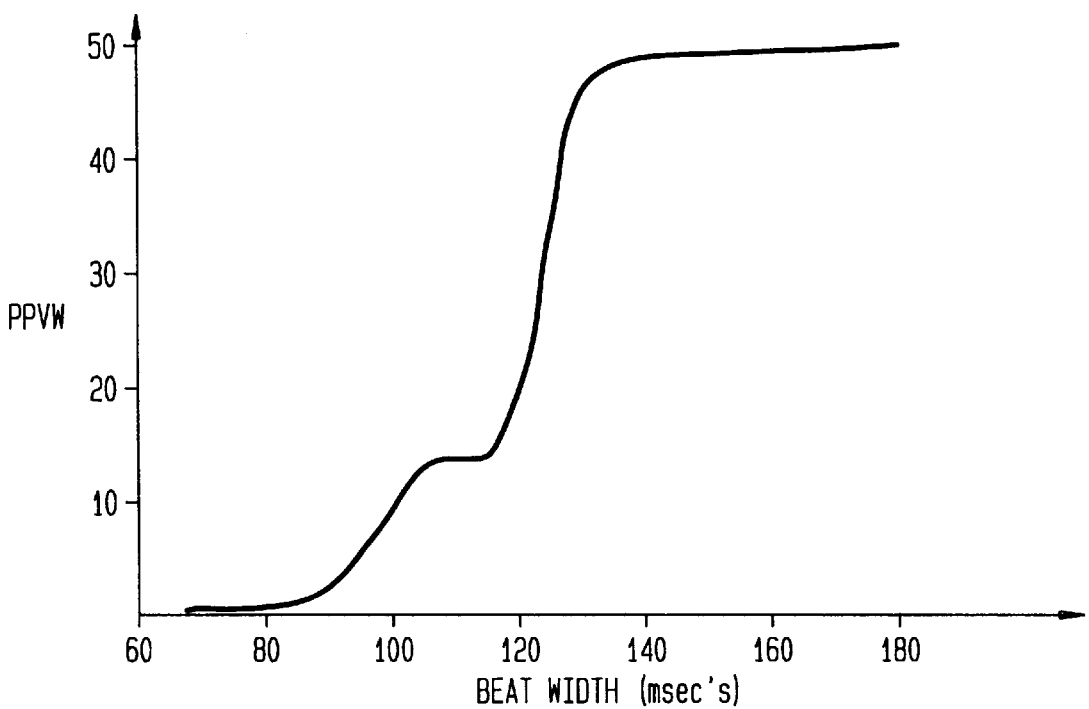
Figure 6:
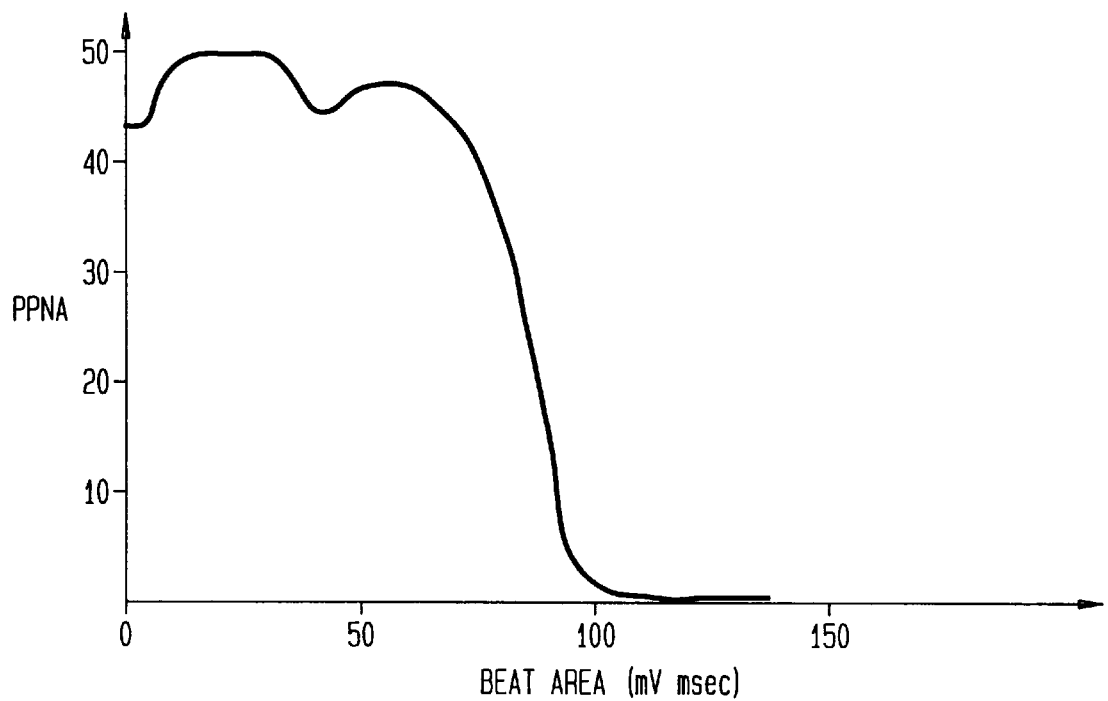
Figure 7:
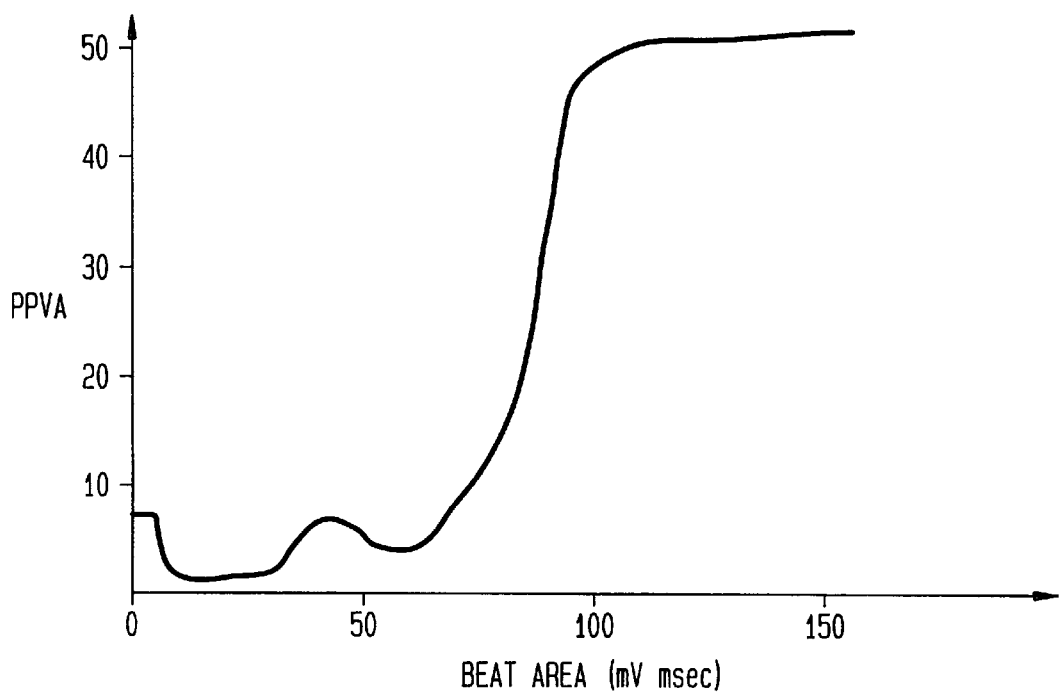

However, in accordance with the present invention, arrhythmia detector 10 is constructed and operates as an expert system, shown generally in FIG. 2 and in more detail in FIG. 3. As shown in FIG. 2, classifier 16 includes a knowledge base 200 and an inference engine 202. The rules are based on a comparison of the features of the detected beat to the features of the current dominant normal (CDN), thereby generating normalized features, and also to some fixed feature values. Each rule for a specific class (e.g., Normal, Ventricular, or X (unknown)) has a certainty factor (CF) associated with it. The present classifier will receive as an input a feature vector which consists of features of each detected beat, each feature having a value associated therewith, such as a width value, an RR-interval value, an area value, a compensatory pause value, a polarity for each detected beat, an indication of shape matching with the shape of the CDN (as shown in FIG. 3), etc. This vector of features is expandable, i.e., additional features can be added or some features can be deleted as desired, and therefore the classifier in accordance with the present invention is extremely flexible.

The output of classifier 16 is a label of the beat as N, V, or X. Additionally, the output can include the certainty associated with each of labels N, V and X.

Quantification Scheme

The expert system classifier of the present invention uses the certainty factor (CF) as a unit of measurement for each feature. The measure of certainty factor, CF[h,e], is a number between 0 and 1 that is a measurement of the belief in a hypothesis h in light of an evidence e. The certainty factor CF[h,e] is defined as the positive predictivity of h given e. The positive predictivity (pp) measure is defined as follows:

$$pp = \frac{TP}{TP + FP},\quad\text{(EQ 1)}$$

where TP is true positive and FP is false positive.

For each evidence e, the hypothesis can be tested on a real annotated database (e.g., the forenoted MIT and AHA databases), and the corresponding CF[h,e]=pp can be determined. This definition of the CF[h,e] is more realistic than the forenoted prior art belief factors which are determined subjectively by the system designer. For example, Let:

h1 be the hypothesis that a beat is a ventricular (V) beat, e1 be the fact that the current beat width (w) is 1.2 times larger than the normal beat width, and pp1 be the positive predictivity of a beat being ventricular based on the evidence e1 from the MIT database.

Then we can write that:

If the current beat width is 1.2 times larger than the normal beat width, then the current beat is a ventricular beat with certainty pp1.

The manner of teaching the knowledge base (the certainty curves of predictivity values for each feature) of the expert system will be described later.

Combining the CF's Associated with Multiple Evidences

If we have more than one evidence, (e1, e2, . . . , ei), with certainty factors (pph(1), pph(2), . . . , pph(i) respectively, supporting a hypothesis h, in accordance with a further aspect of the invention the certainty factors are combined in accordance with the following technique, illustrated as a program, to generate a total certainty factor cfh supporting the hypothesis h.

```
cfh=0; this represents initialization.           (EQ 2)
``` for k=1:N; this represents the amount of evidences (features).

cfh=cfh+pph(k)*(1−cfh). end where N is the total number of evidences.

Returning again to FIG. 2, illustrated therein is the application of the Beat Width and RR interval features to knowledge base 200 (for brevity, the full set of applied features are not illustrated until FIG. 3). In response, portion 204 of knowledge base 200, which knows the membership functions (MSF) for Beat Width values of Normal beats (as continuous curves of positive predictivity), provides at its output a Certainty Factor for the current beat being Normal which is based on the value of the input Width Factor. In a similar manner, portion 206 of knowledge base 200 provides at its output a Certainty Factor for the current beat being Normal based on the value of the input RR interval Factor. Similarly, portions 208 and 210 of knowledge base 200 provide at their respective outputs a Certainty Factor for the current beat being Ventricular based on the value of the input Beat Width and RR interval Factors, respectively. As will be described in greater detail in conjunction with FIG. 3, portions 212 and 214 calculate the total certainty factor for the current beat being a normal and a ventricular beat, respectively, based on the certainty factor values provided to them by portions 204,206 and 208,210, respectively. Finally, as will also be described in greater detail in conjunction with FIG. 3, portion 216 decides the beat label based on the total certainty factor calculated for each label.

As shown in FIG. 3, beat classifier 16 receives a set of QRS features as inputs and generates a beat label N, V or X as an output. The abbreviations used for the beat classifier inputs are as follows: Current Beat Width (Wc), Current Beat Area (Ac), Current Beat Amplitude (AMc), Current Beat Polarity (Pc), Current Beat ST-Area (ATc), Current Beat ST-Polarity (PTc), Current Beat R-R interval (RRc), Beat Wave Shape Match (correlation factor) with all Templates (WSM). The outputs of classifier 16 are as follows: Normal Beat Label (N), Ventricular Beat Label (V), and Unknown or Artifact Beat Label (X).

More specifically, an averager 300 keeps a current, i.e., updated, average of the Normal features when the current beat is confirmed to be Normal by the beat classifier. The update command is provided by line 302 when a Normal beat is determined. The averaging technique that is used for determining the average value for the Normal Width ($W_n$), Area ($A_n$), Amplitude ($AM_n$), Polarity ($P_n$), ST-Area ($AT_n$), ST-Polarity ($PT_n$) and R-R interval ($RR_n$) is as follows:

Average Normal Feature=($11/12$) Average Normal Feature+($1/12$) New Feature.

Additionally, when a reset command (not specifically shown) is provided to averager 300, all the averaged Normal features are set to the values of the features of the first Normal beat that is received.

A feature factor calculator 304 is a type of normalizer, in that it calculates a relative feature factor for each of the following features: Width, Area, Amplitude and ST-Area, as follows, Feature Factor=New Feature/Average Normal Feature.

The Feature Factor for Beat Polarity and ST-Polarity is calculated as follows,

Feature Factor=Current Polarity−Average Normal Polarity

As shown in FIG. 3, the above-noted feature factors, as well as several fixed feature values, namely Beat Width, Beat Area and Beat Wave Shape Match are then applied to the knowledge base where certainty factors for each of the features, for each of the possible labels, are determined.

Before describing how the knowledge base is used, description will now be provided of how the knowledge base is acquired. As previously noted a set of MIT-BIH database tapes are selected as a representative set of normal and ventricular beat morphologies. An automated statistical program takes as its input feature values and labels of the beats corresponding to these features, and generate continuous curves of certainty for the beats being normal and ventricular based on the values of these features.

This process may be explained by the following example: let's say we are looking at the feature "Beat Width" in msecs. The widths of all the beats in the selected set of data for training are extracted. The range of width the statistical program examines is determined to be zero to 300 msecs, in increments of 10 msecs. The statistical program starts by looking in the range of 0 to 10 msecs, looks at these beat labels, counts the normal beats and ventricular beats which have width in this range, and calculates the first point on a PPNW curve (a curve of positive predictivity values of a beat being Normal based on the value of the beat width feature), and then the first point on a PPVW curve (a curve of positive predictivity values of a beat being Ventricular based on the value of the beat width feature).

The first point, PPNW(1), on the PPNW curve is calculated as follow:

$$PPNW(1)=TPN/TPN+TPV;$$

where, TPN represents the total number of normal beats of width between 0 and 10 msecs, and TPV represents the total number of normal beats of width between 0 and 10 msecs.

The first point PPVW(1) on the PPVW curve is calculated as follow:

$$PPVW(1)=TPV/TPN+TPV.$$

Next, the statistical program examines the above process in the range 10 to 20 msecs to find the second points on the PPNW and PPVW curves. In general, the i-th points on the PPNW and PPVW curves are determined similar to the above, as follow:

$$PPNW(i)=TPN/TPN+TPV;$$

$$PPVW(i)=TPV/TPN+TPV.$$

where, TPN represents the total number of normal beats of width between i*10 and (i+1)*10 msecs, and TPV represents the total number of normal beats of width between i*10 and (i+1)*10 msecs.

For each of the illustrated features, the statistical program uses the same approach to derive certainty curves (sometimes called membership functions) corresponding to each of the features. These certainty curves are shown by FIGS. 4–23.

The following table shows the features used in the FIG. 3 embodiment of the invention, and the corresponding abbreviations used in FIGS. 4–23.

| Feature | Beat Certainty Curve for Normal | Beat Certainty Curve for Ventricular |
|---|---|---|
| Beat Width in msecs | PPNW | PPVW |
| Beat Area in mV*secs | PPNA | PPVA |
| Beat Width Factor (current beat width/ normal beat width) | PPNWF | PPVWF |
| Beat Area Factor(current beat area/normal beat area) | PPNAF | PPVAF |
| Beat Amplitude Factor (current beat amplitude/normal beat amplitude) | PPNAM | PPVAM |
| ST-Wave Area Factor (current beat ST-Wave Area/normal beat ST-Wave Area) | PPNTA | PPVTA |
| ST-Wave Polarity (current beat ST-Wave Polarity/ normal beat ST-Wave Polarity) | PPNTP | PPVTP |
| Beat Polarity (abs(Current Beat Polarity - Normal Beat Polarity) | PPNP | PPVP |
| R-to-R Interval (Current Beat R-to-R interval/Normal Beat R-to-R interval) | PPNRR | PPVRR |
| Beat Match to Normal Beat | PPNM | PPVM |

Block 306 of FIG. 3 is responsive to the outputs of block 304, as well as the fixed feature values for Beat Width, Beat Area and Beat Match, for determining a total Certainty Factor for each beat being a Normal, Ventricular and an unknown (X) beat.

The total certainty factor for a beat being a Normal is determined as follows:

ppn(1)=find-membership (PPNWF, WIDTH-FACTOR, width_factor)/100;

ppn(2)=find-membership (PPNAF, AREA-FACTOR, area-factor)/100;

ppn(3)=find-membership (PPNA, BEAT-AREA, beat-area)/100;

ppn(4)=find-membership (PPNW, BEAT-WIDTH, beat-width)/100;

ppn(5)=find-membership (PPNAM, AM-FACTOR, amplitude-factor)/100;

ppn(6)=find-membership (PPNTA, TWAVE-AREA-FACTOR, st-area-factor)/100;

ppn(7)=find-membership (PPNTP, TWAVE-POLARITY, abs (PTc−PTn))/100;

ppn(8)=find-membership (PPNP, POLARITY-VAL, abs (Pc−Ppn))/100;

ppn(9)=find-membership (PPNM, BEAT-MATCH, WSMNc)/100;

The total certainty factor of a beat being Normal (cfn) is calculated in accordance with the program:

cfn=0; initialization for k=1:9 cfn=cfn+ppn(k)*(1−cfn); end

Figure 8:
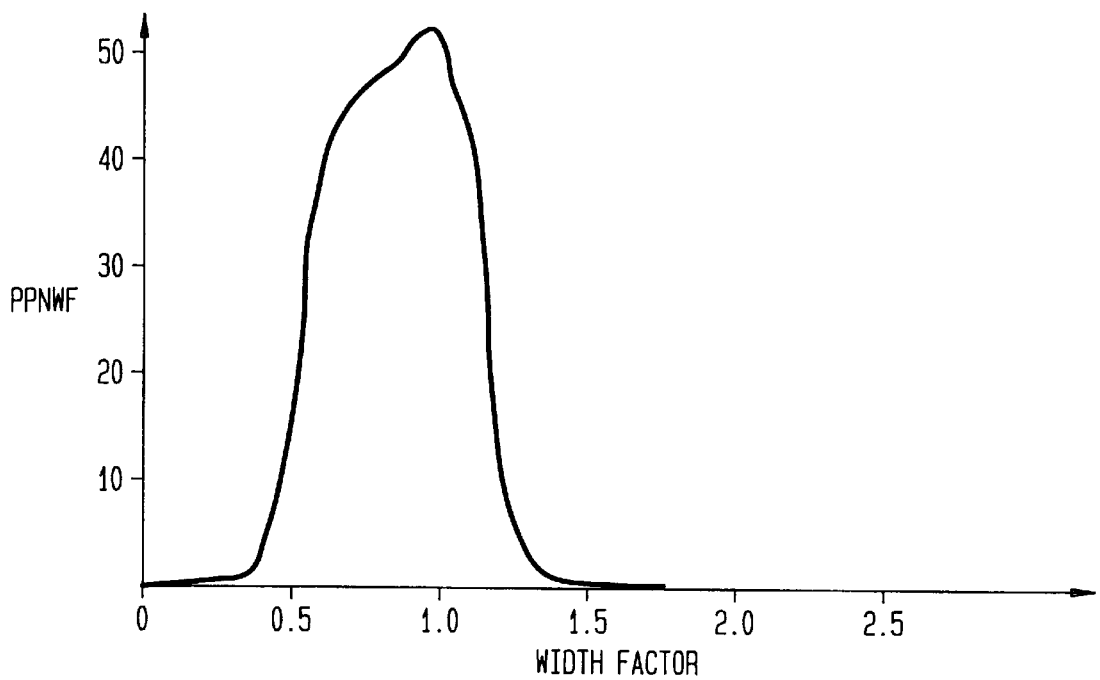

For purpose of illustration it is now described how ppn(1) is found using the above process. Find-membership (PPNWF,WIDTH-FACTOR, width-factor) will look at the curve PPNWF in FIG. 8 to determine ppn(1). If we assume that the width-factor=1.2, then find-membership will look at the WIDTH-FACTOR-axis to find the 1.2 point, and then find the PPNWF curve point value that corresponds to 1.2 on the WIDTH-FACTOR-axis. As shown in FIG. 8, the value for ppn(1)=8 for a width-factor of 1.2.

The same technique is also used to determine the rest of the ppn(i)'s. Basically, find-membership (CURVE, X, x) maps the x on the X-axis, and then finds the point of intersection of a vertical line taken from x on the X-axis to the CURVE, and assigns the value of this point of intersection to the value of ppn(i).

Similarly, the total certainty factor for a beat being a Ventricular is determined as follows:

ppv(1)=find-membership (PPVWF, WIDTH-FACTOR, width-factor)/100;

ppv(2)=find-membership (PPVAF, AREA-FACTOR, area-factor)/100;

ppv(3)=find-membership (PPVA, BEAT-AREA, beat-area)/100;

ppv(4)=find-membership (PPVW, BEAT-WIDTH, beat-width)/100;

ppv(5)=find-membership (PPVAM, AM-FACTOR, amplitude-factor)/100;

ppv(6)=find-membership (PPVTA, TWAVE-AREA-FACTOR, st-area-factor)/100;

ppv(7)=find-membership (PPVTP, TWAVE-POLARITY, abs (PTc−PTn))/100;

ppv(8)=find-membership (PPVP, POLARITY-VAL, abs (Pc−Ppn))/100;

ppv(9)=find-membership (PPVM, BEAT-MATCH, WSMNc)/100;

The total certainty factor of a beat being Ventricular (cfv) is calculated in accordance with the program:

cfv=0; initialization for k=1:8 cfv=cfv+ppv(k)*(1−cfv); end

Figure 9:
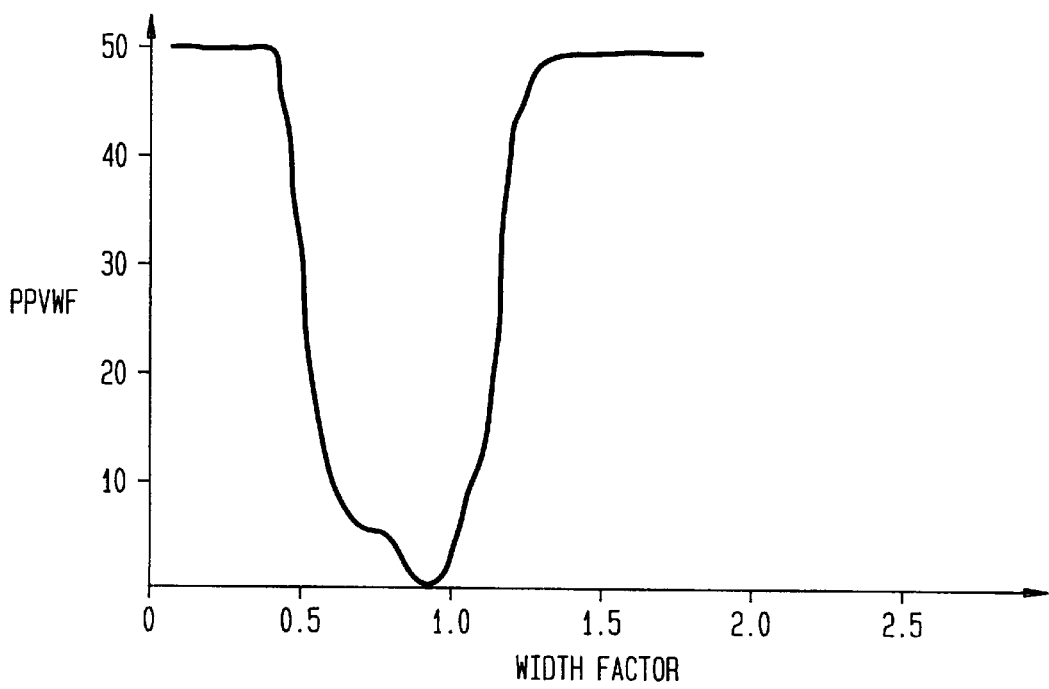
Figure 10:
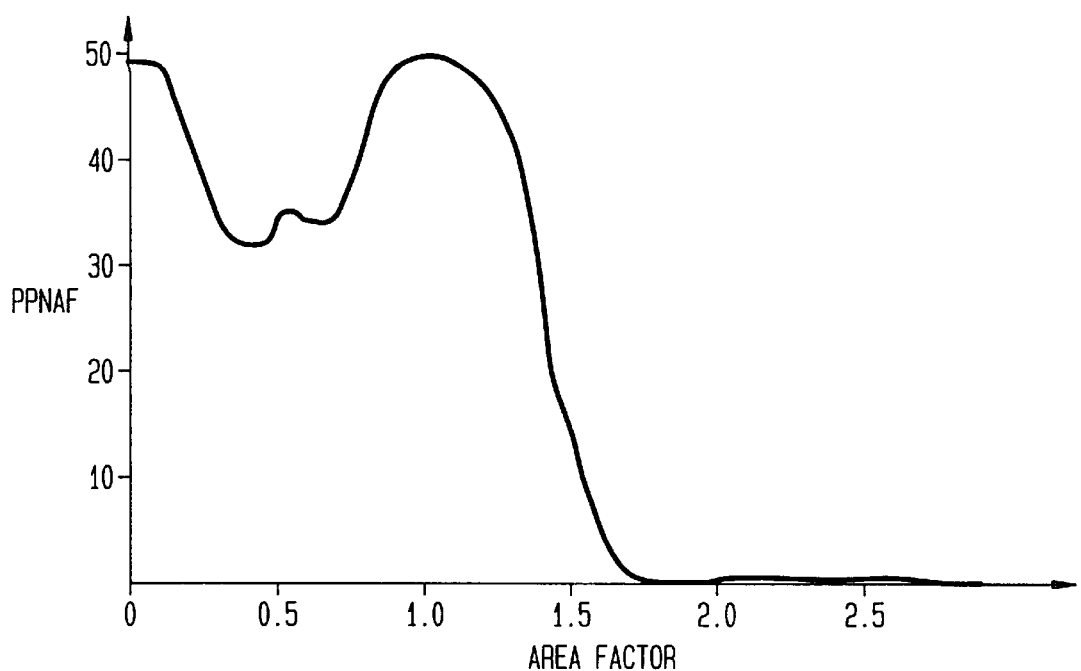
Figure 11:
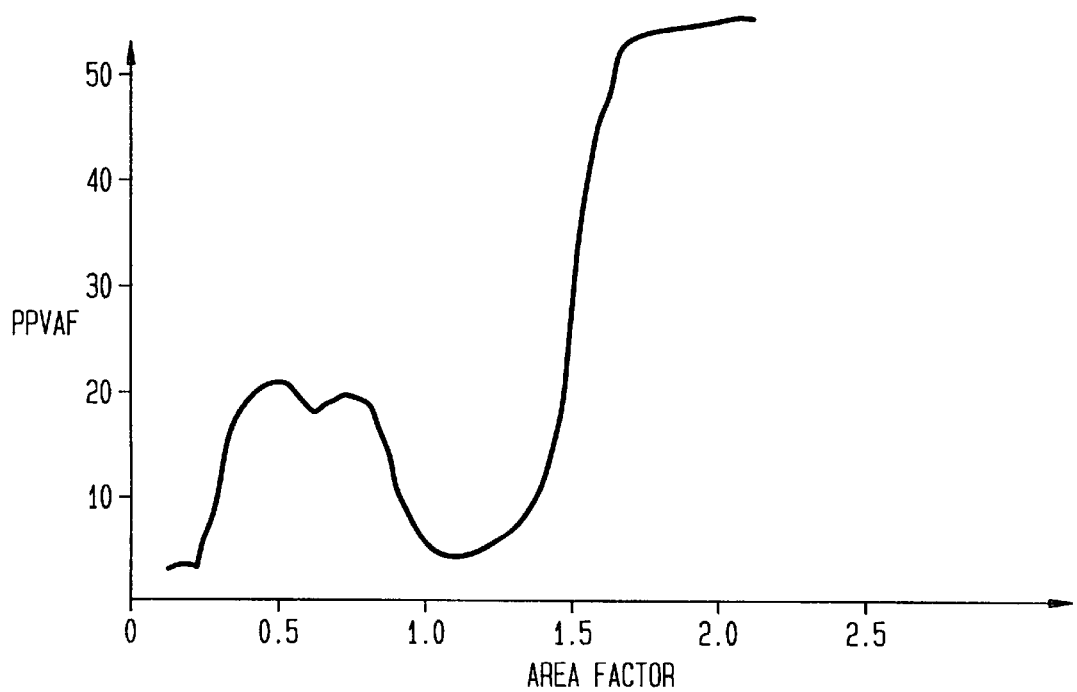
Figure 12:
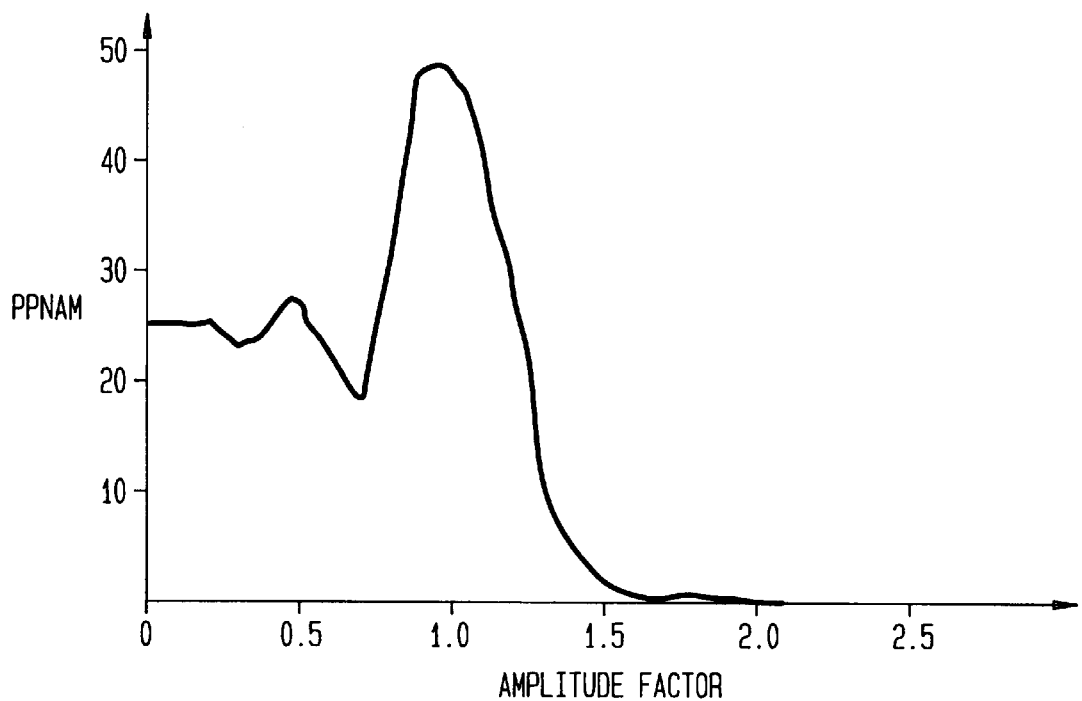
Figure 13:
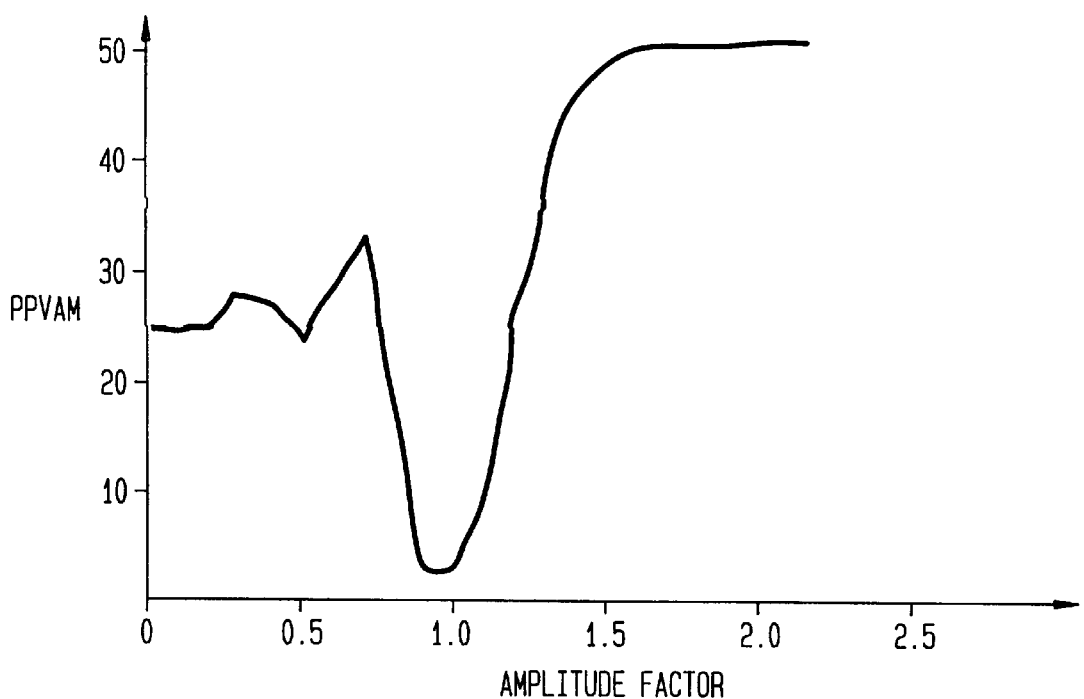
Figure 14:
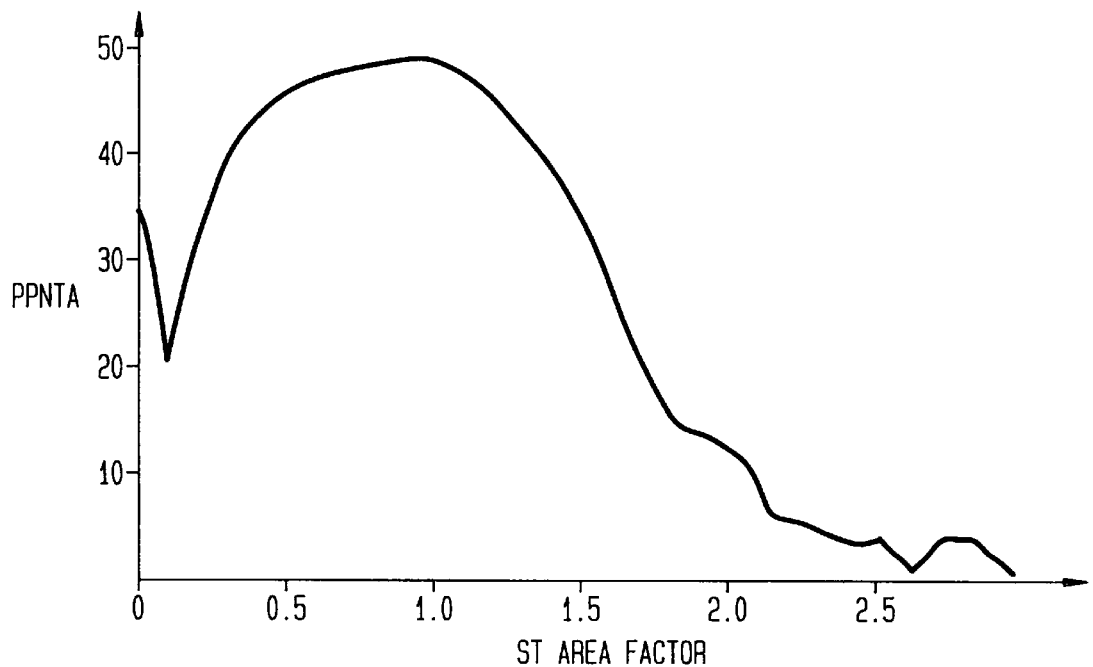
Figure 15:
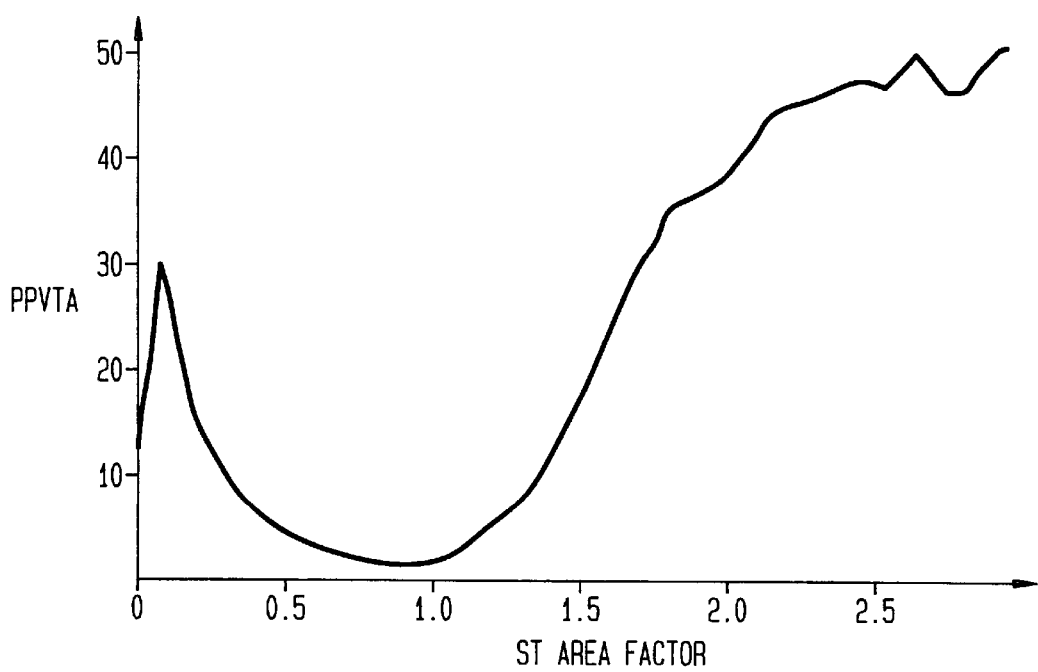
Figure 16:
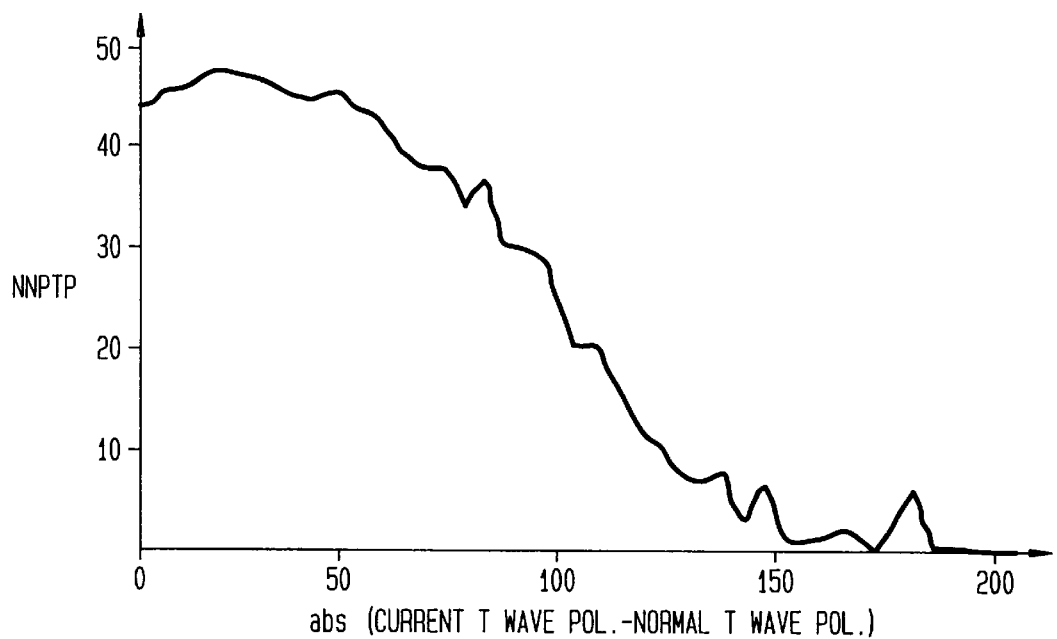
Figure 17:
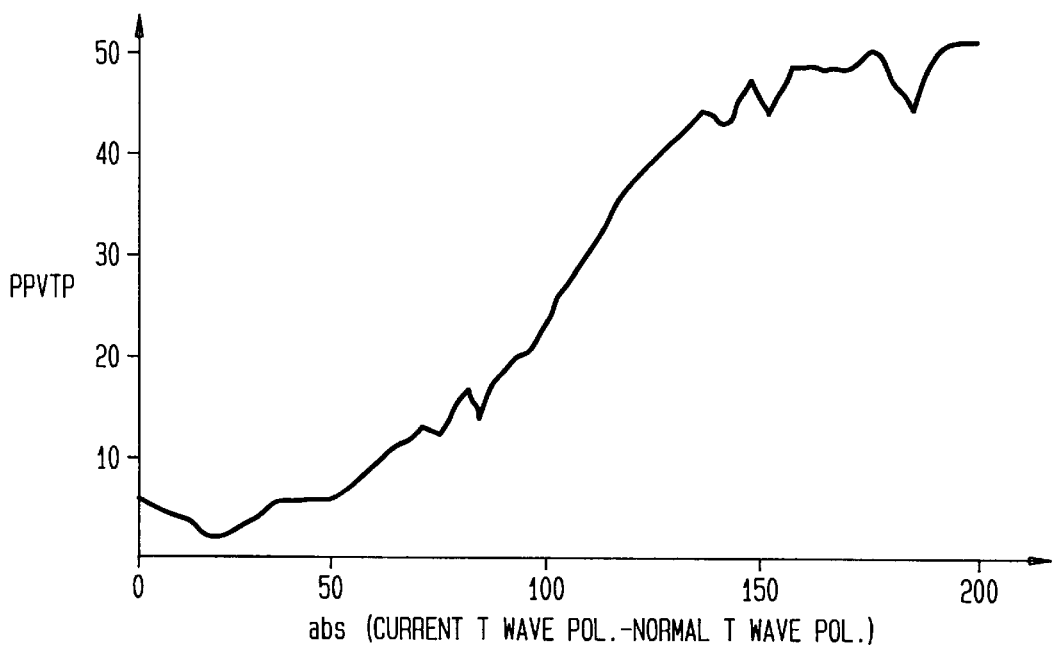
Figure 18:
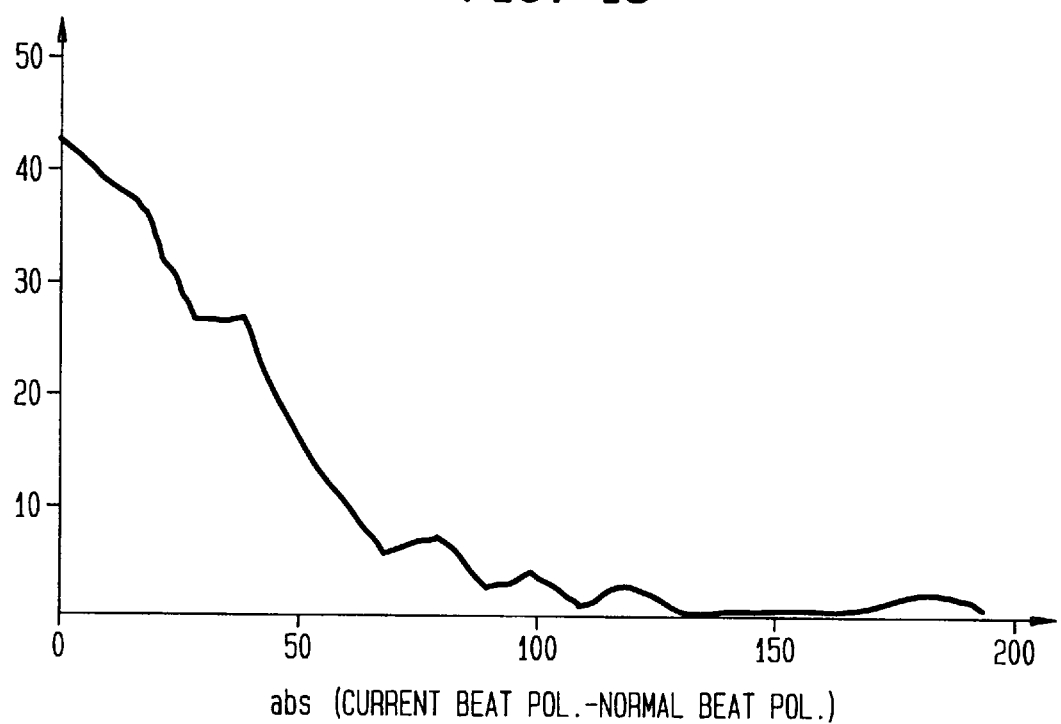
Figure 19:
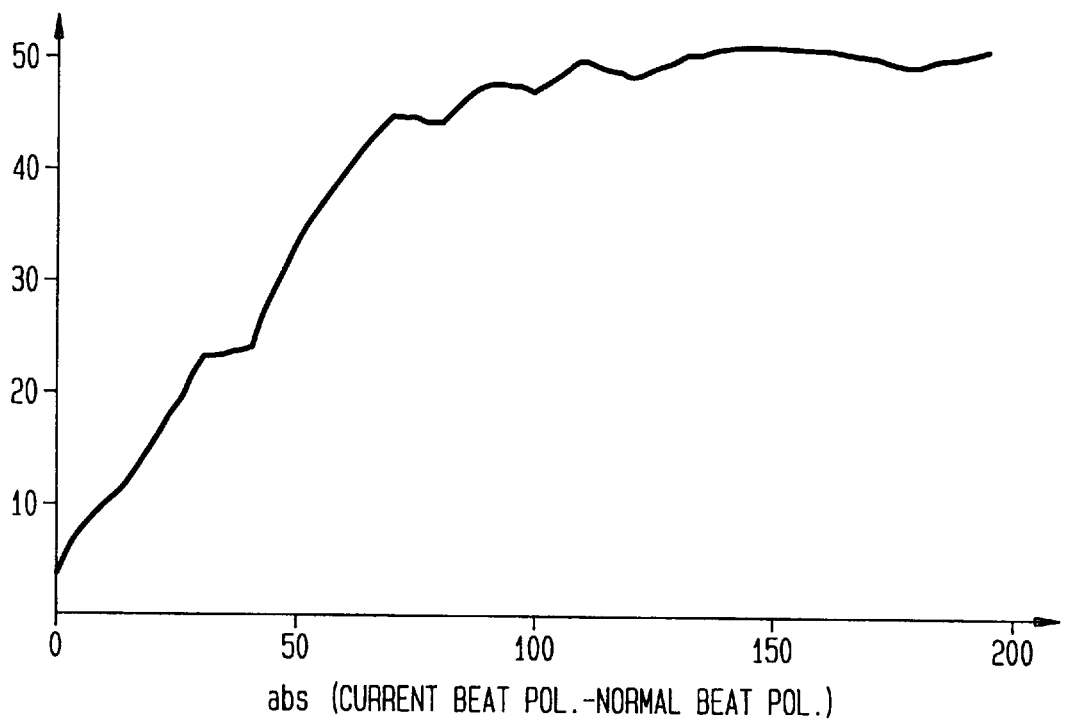
Figure 20:
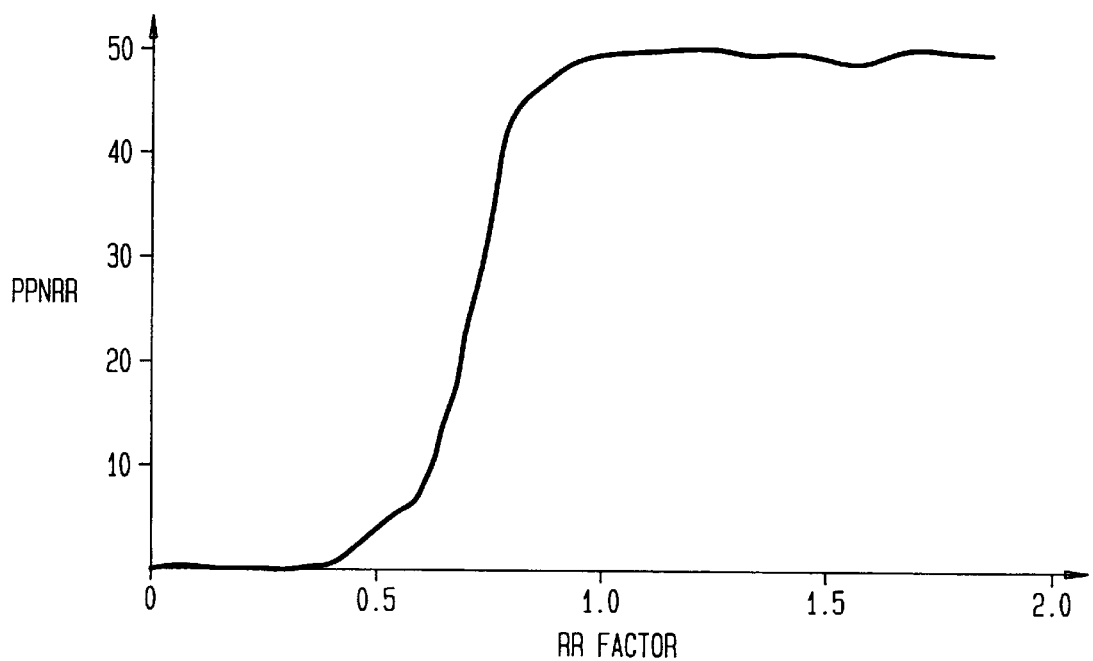
Figure 21:
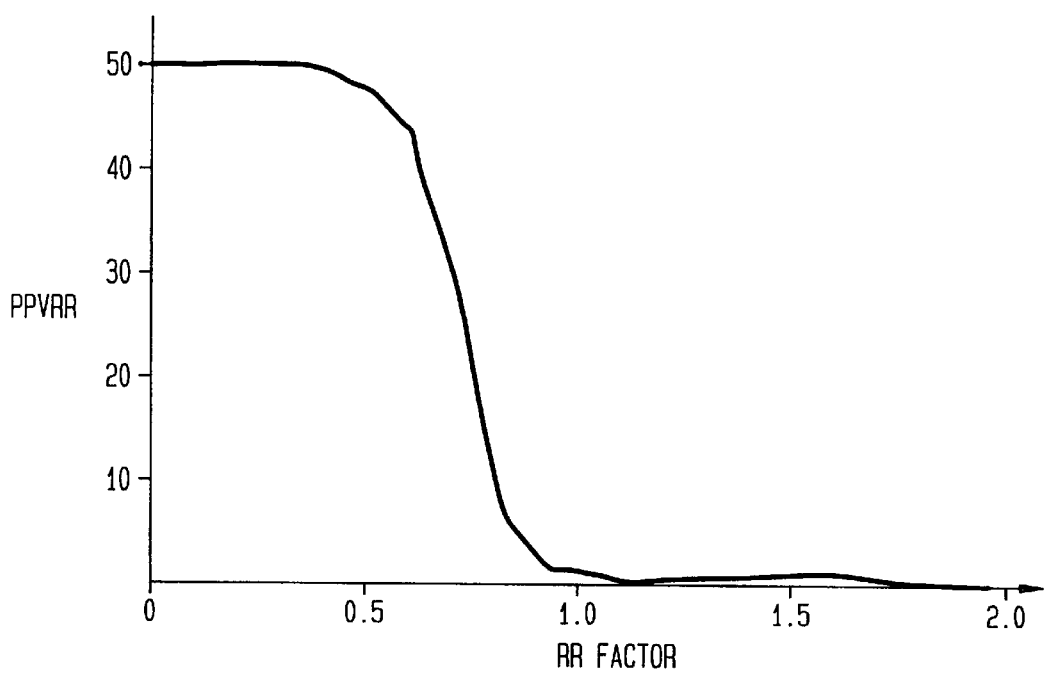
Figure 22:
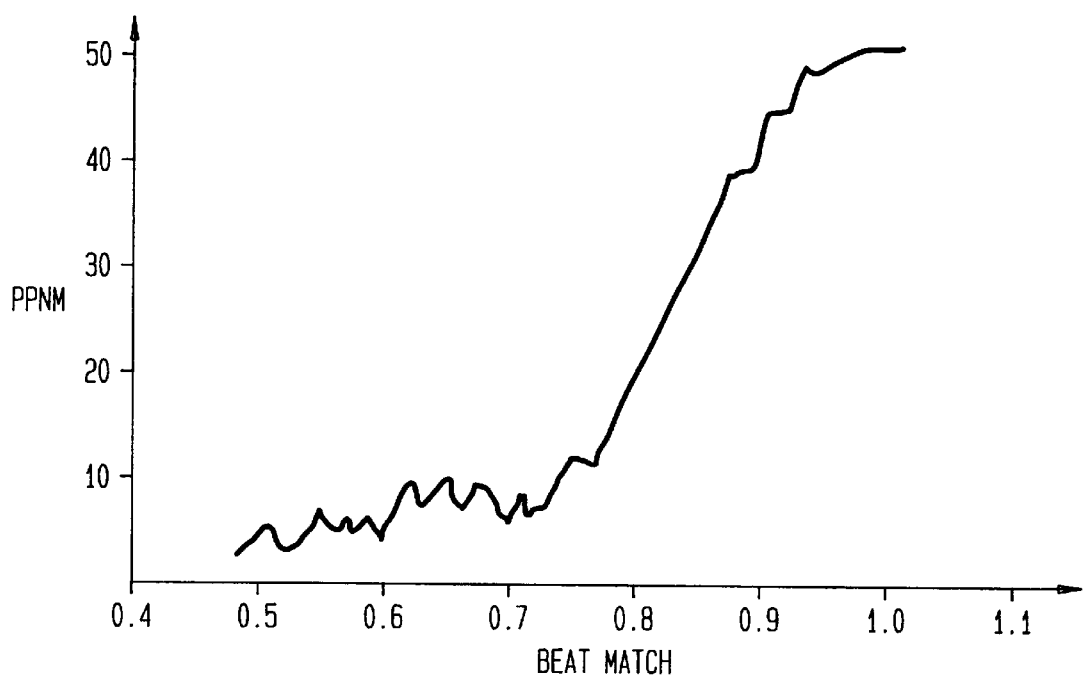
Figure 23:
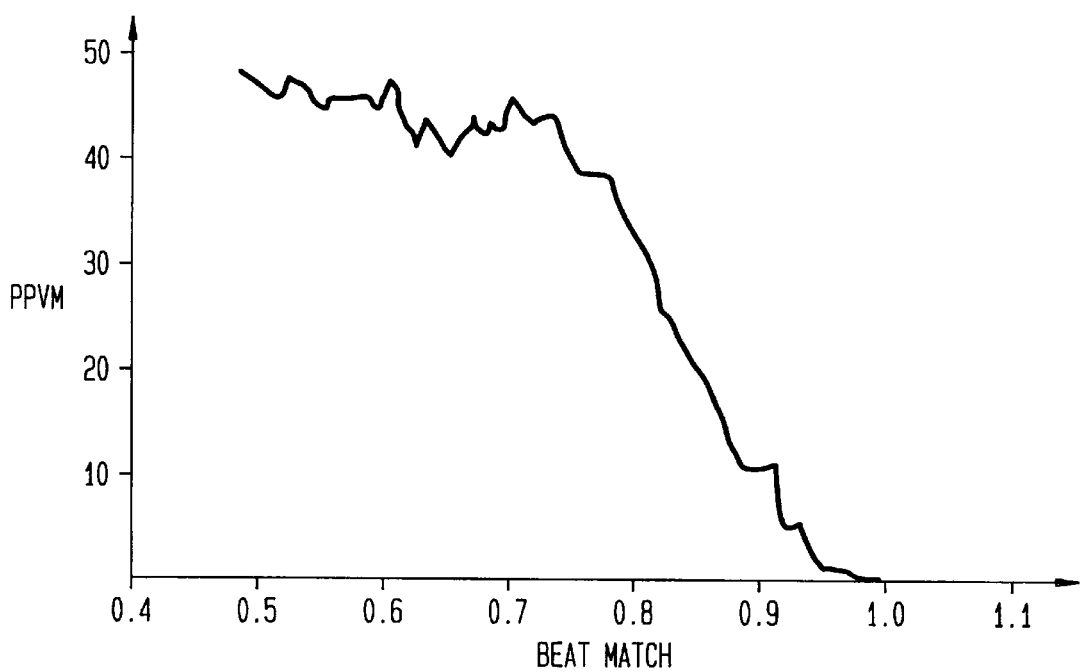

For purpose of illustration it is now described how ppv(1) is found using the above process. Find-membership (PPVWF,WIDTH-FACTOR, width-factor) will look at the curve PPVWF in FIG. 9 to determine ppv(1). If we assume that the width-factor=1.2, then find-membership will look at the WIDTH-FACTOR-axis to find the 1.2 point, and find the PPVWF curve point value that corresponds to 1.2 on the WIDTH-FACTOR-axis. As shown in FIG. 9, this value is ppv(1)=42 for a width-factor of 1.2.

The same technique is also used to determine the rest of the ppv(i)'s. Basically, find-membership (CURVE, X, x) maps the x on the X-axis, and then finds the point of intersection of a vertical line taken from x on the X-axis to the CURVE, and then assign this the value of this point of intersection to the value of ppv(i).

For determining an Unknown or Artifact (X) Certainty Factor, the following rules are used:

1. If [Wc>10*Wn], then current beat is an X with ppx(1)=0.7
2. If [Ac>10*An], then current beat is an X with ppx(2)=0.7
3. If [RRc<0.5*RRn], then current beat is an X with ppx(3)=0.5
4. If [Wc>300 msecs], then current beat is an X with ppx(4)=0.9
5. If [Ac>200 mv*msecs], then current beat is an X with ppx(5)=0.7

NOTE: More rules can be added as desired.

The total certainty factor of a beat being Unknown (cfx) is calculated in accordance with the program:

cfx=0; initialization for k=1:5 cfx=cfx+ppx(k)*(1−cfx); end

Finally, block 308 decides the beat label, which, in accordance with one aspect of the present invention, is based on the total certainty factor calculated for each label. In the illustrated embodiment, for the generation of the N, V and X labels, the following logic is used:

```
if cfv > cfn and cfv > cfx, and
    if current beat has been seen more than MIN_NUMBER (=1) of times, then
    current beat is Ventricular (V)
    else
    current beat is Questionable (Q)
    end
else, if cfn > cfv and cfn > cfx
    current beat is Normal (N)
else, if cfx > cfn and cfx > cfv
    current beat is Unknown or Artifact (X)
end
```

Thus, what has been shown and described is a classifier for an unknown input which fulfills all the advantageous and objects sought therefore. Many changes, modifications, variations and other uses and applications of the subject invention will however be apparent to those of ordinary skill in the art after consideration of this specification and its accompanying drawings which disclose a preferred embodiment thereof. For example, although in the illustrated embodiment the certainty factors (CF's) for a given hypothesis h were determined in a rather direct, simple, manner, in accordance with an alternative embodiment of the present invention, different manners of determining the certainty factors can be used. For example, one can combine the CF of the hypothesis with the CF of the evidence itself. That is, if the certainty factor of a hypothesis h in the light of evidence e is CF'[h,e], and the certainty factor of evidence e being true in the light of evidence E is CF[e,E], then the certainty factor of this hypothesis h given evidence e has some uncertainty associated with it, as shown below:

$$CF[h,e]=CF'[h,e]*CF[e,E] \quad (EQ\ 3)$$

Example: Assume that the certainty factor of a beat being a V, when the current beat width is equal to 1.2 times the width of normal beat, is pp1=0.6. Also assume that we are only pp2=0.8 certain that the current beat width is equal to 1.2 times the normal beat width. Then we can rewrite the above situation as follows:

h: hypothesis that current beat is a ventricular (V) beat e: current beat width is equal to 1.2 times the current dominant normal width E: certainty that current beat width is equal to 1.2 times the normal beat width The certainty factor that the current beat is a ventricular beat given that its width is equal to 1.2 times the normal beat is width is: CF'[h,e]=0.6; and the certainty factor that current beat width is equal to 1.2 times the normal beat width is: CF[e,E]=0.8.

Then, the certainty factor that current beat is a ventricular beat is:

$$CF[h,e]=CF'[h,e]*CF[e,E]=0.6*0.8=0.48.$$

It is also possible that it may be desirable to have changing functions for evidence. That is, in some cases a certain evidence (or feature) does not support the hypothesis as well as it does in other cases. In this case the evidence will have two different certainty factors associated with it:

CF[h,e]=pp1 if E is present; and

CF[h,e]=pp2 if E is absent.

For example, in the case of ECG analysis, the earliness of a beat will have a higher certainty factor in support of the hypothesis that this beat is Ventricular in a normal sinus rhythm than in an atrial flutter or fibrillation rhythm.

We can formulate the above as follows:

Let:

h1: hypothesis that a beat is ventricular e1: beat is early

E1: rhythm is atrial fibrillation or flutter

!E1: rhythm is not atrial fibrillation nor flutter

CF[h1,e1,E1]=pp1

CF[h1,e1,!E1]=pp2

As an illustrative example, pp1 can be equal to 0.1 while pp2 can be equal to 0.5. However, the certainty factor CF[h1,e1,E1] will be determined from a data set where atrial flutter and fibrillation are absent, and CF[h1,e1,!E1] will be determined from a data set where atrial flutter or fibrillation is present.

Furthermore, features from other signals such as a saturated oxygen signal (SPO2) and an invasive blood pressure signal can be used as inputs to this classifier to aid in ECG beat classification. Some of the features from SPO2 are: beat width, beat amplitude and beat-to-beat interval. Some of the features from invasive blood pressure (IBP) signals are: beat width, beat amplitude, beat-to-beat interval, systolic pressure, diastolic pressure and mean pressure. For each feature that is added, a certainty factor set of curves has to be learned from a training data set.

Additionally, an engine of the same nature as the one described above for ECG beat classification can be used, for example, for ECG rhythm analysis, smart alarms, SPO2 measurements and IBP measurements.

Some of the inputs to this engine for ECG rhythm analysis would be: R-to-R interval, Beat match to the dominant normal, beat match to the seen ventricular beats, beat width, beat amplitude, beat area, beat polarity, ST-area, ST-polarity, SPO2 features (beat width, beat amplitude, beat-to-beat interval), invasive blood pressure features (beat width, beat amplitude, beat-to-beat interval, systolic pressure, diastolic pressure, mean pressure), frequency power spectrum of ECG signals, noise estimate on each ECG lead, and noise estimate on the SPO2 and IBP signals. The output of this engine is the ECG rhythm: normal sinus rhythm, bigeminy, trigeminy, ventricular couplet, accelerated ventricular rhythm, run, ventricular tachycardia run, ventricular fibrillation, and atrial fibrillation.

Some of the inputs to this engine for smart alarms would be: ECG beat label, ECG rhythm, systolic pressure, diastolic pressure, mean pressure, blood oxygen saturation, heart rate, respiration rate, etCO2 pressure, noise estimate on each ECG lead, and noise estimate on the SPO2 and IBP signals. The output of this engine is an alarm to alert the clinical staff.

Some of the inputs to this engine for SPO2 measurements would be: ECG beat label, systolic pressure, diastolic pressure, mean pressure, heart rate, respiration rate, etCO2 pressure, invasive blood pressure features (beat width, beat amplitude, beat-to-beat interval, systolic pressure, diastolic pressure, mean pressure), noise estimate on each ECG lead, and noise estimate on the SPO2 and IBP signals. This engine would make a decision based on these inputs if the current beat is normal, abnormal, or artifact. In the case of normal beat, oxygen saturation would be measured. The outputs of this engine are: oxygen saturation and pulse rate.

Some of the inputs to this engine for IBP measurement would be: ECG beat label, heart rate, respiration rate, SPO2 features (beat width, beat amplitude, beat-to-beat interval), noise estimate on each ECG lead, and noise estimate on the SPO2 and IBP signals. This engine would make a decision based on these inputs if the current beat is normal, abnormal, or artifact. In the case of normal and abnormal beats, systolic, diastolic, and mean pressures would be measured. The outputs of this engine are: systolic pressure, diastolic pressure, mean pressure, and pulse rate.

For each feature that is used in each of the above-described alternative embodiments, a certainty factor set of curves has to be learned from a training data set.

In view of the above, the scope of the invention is intended to be limited only by the following claims.

I claim:

1. A method for classifying an input as belonging to one of a plurality of predefined classes, comprising:
    (a) developing a plurality of feature values and forming a feature vector from the feature values which is representative of the input;
    (b) directly deriving curves of predictivity values from a reference database of inputs having pre-existing class annotations, to produce a knowledge base of principally learned classification information;
    (c) applying the feature vector to the knowledge-base for developing a plurality of predictivity values for each feature, each predictivity value being indicative of a likelihood of the input belonging to a respective one of each of said classes based on the feature value;
    (d) combining the predictivity values developed for each of the features for each class to generate a total predictivity value for each class; and
    (e) generating a determination of class based upon the total predictivity values generated by the prior step.

2. The method according to claim 1, wherein said determination of class is made by comparing the total positive predictivity value determined for each class and selecting as the determined class that class having the greatest positive predictivity value.

3. The method according to claim 1, further including the steps of:
    developing a normal value for at least one of the features using prior values of said feature that have previously been classified as normal; and
    developing a normalized feature for use in step (c) above, using the normal value determined for that feature.

4. The method according to claim 1, wherein the input is representative of a waveform.

5. The method according to claim 4, wherein one of said features is a shape feature which is compared with a predefined waveform shape for each of the classes and the result of the comparison is used as a feature in step (c).

6. The method according to claim 4, wherein said input comprises an EKG waveform of a patient being monitored, and said feature vector comprises a plurality of values representative of measurements of various attributes of said EKG waveform.

7. The method according to claim 6, wherein said various attributes of said EKG waveform comprise at least beat width, beat area and RR interval.

8. The method according to claim 6, wherein said various attributes of said EKG waveform comprise normalized measurements of the attributes, said normalization being a comparison of the attributes values of the current EKG waveform with the current dominant normal values for these attributes.

9. The method according to claim 6, wherein said input also includes as feature values measurement values of various attributes of a heartbeat signal generated using pulse oximetry.

10. The method according to claim 6, wherein said input also includes as feature values measurement values of various attributes of a heartbeat signal generated using a blood pressure measurement technique.

11. The method according to claim 6, wherein in step 1(e) said class determination is an EKG rhythm, such as normal sinus rhythm, bigeminy, trigeminy, fibrillation and tachycardia.

12. The method according to claim 4, wherein step 1(e) determines a class from the group of classes including at least normal and ventricular.

13. The method according to claim 4, wherein in step 1(e) said class determination is an alarm for a patient monitoring apparatus, and said input vector is representative of a plurality of physiological conditions of a patient being monitored, said conditions including EKG rhythm, blood pressure measurements and pulse oximetry measurements.

14. The method according to claim 4 for use in a patient monitoring system, wherein in step 1(d) said class determination is used as a validation of the measurement of a physiological condition of a patient being monitored.

15. The method according to claim 14, wherein said validation comprises the classification of the input as normal, and is used to validate the determination of the pulse rate and oxygen saturation of said patient using pulse oximetry.

16. The method according to claim 14, wherein said validation comprises the classification of the input into a known classification, such as as normal or abnormal, and is used to validate the determination of blood pressure values obtained from a patient using an invasive blood pressure monitoring technique.

17. The method according to claim 1, wherein in step (c) the predictivity value is modified based upon the certainty of the feature value being accurate.

18. The method according to claim 1, wherein in step (c) the predictivity value used for a given feature value is determined not only by the value of the feature, but also on the existence of an external condition.

19. The method according to claim 18, wherein said feature value is a measurement of the RR interval in a given portion of an EKG waveform, and said external condition is the presence of an atrial fibrillation rhythm in that portion of the EKG waveform.

20. The method according to claim 1, wherein step 1(d) develops a normalized summation of the predictivity values developed for each feature of each class.

21. The method according to claim 20, wherein step 1(d) develops said normalized summation in accordance with the following equation:

$$cfh = cfh + pph(k)*(1-cfh), \text{ for } k=1:N,$$

where cfh=0 upon initialization, and where N represents the total amount of evidences (features).

22. An apparatus for classifying an input as belonging to one of a plurality of predefined classes, comprising:

extracting means responsive to an input signal for extracting a plurality of features therefrom and developing therefore a corresponding plurality of feature values, and forming a feature vector from the feature values which is representative of the input signal;

a learning means for directly deriving curves of predictivity values from a reference database of inputs having pre-existing class annotations, thereby producing a knowledge-base of principally learned classification information;

applying means for applying the feature vector to the knowledge base for developing at its output a plurality of predictivity values for each feature value of the feature vector, each predictivity value being indicative of a likelihood of the input belonging to a respective one of each of said classes based on the feature value;

a combining means responsive to said plurality of predictivity values for combining the predictivity values developed for each of the features for each class, and generating a total predictivity value for each class; and determining means for generating a determination of class based upon the total predictivity values generated by the combining means.

23. Apparatus according to claim 22, wherein said determining means includes comparing means for comparing the total predictivity value determined for each class and selecting as the determined class that class having the greatest predictivity value.

24. Apparatus according to claim 22, wherein said input signal comprises an EKG waveform of a patient being monitored, and said extracting means develops as said feature vector a plurality of values representative of measurements of various attributes of said EKG waveform.

25. Apparatus according to claim 24, wherein said extracting means includes means for developing values for at least beat width, beat area and RR interval.

26. Apparatus according to claim 24, further including normalization means for developing normalized measurements of the attributes of said EKG waveform, said normalization means including means for comparing the attribute values of the current EKG waveform with average normal values for these attributes.

27. Apparatus according to claim 22, wherein said combining means comprises a summation means for developing a normalized summation of the predictivity values developed for each feature of each class.

28. Apparatus according to claim 27, wherein said combining means develops said normalized summation in accordance with the following equation:

$$cfh = cfh + pph(k)*(1-cfh), \text{ for } k=1:N,$$

where cfh=0 upon initialization, and where N represents the total amount of evidences (features).

* * * * *